United States Patent
Gujarathi et al.

(10) Patent No.: US 10,395,010 B2
(45) Date of Patent: Aug. 27, 2019

(54) CLOUD-BASED BLOOD BANK COLLABORATIVE COMMUNICATION AND RECOMMENDATION

(71) Applicant: International Business Machines Corporation, Armonk, NY (US)

(72) Inventors: Nilesh R. Gujarathi, Pune (IN); Sachchidanand Singh, Pune (IN); Sanjay K. Singh, Pune (IN); Vikram V. Sutar, Pune (IN)

(73) Assignee: International Business Machines Corporation, Armonk, NY (US)

( * ) Notice: Subject to any disclaimer, the term of this patent is extended or adjusted under 35 U.S.C. 154(b) by 166 days.

(21) Appl. No.: 15/194,616

(22) Filed: Jun. 28, 2016

(65) Prior Publication Data

US 2017/0053067 A1    Feb. 23, 2017

Related U.S. Application Data

(63) Continuation of application No. 14/828,576, filed on Aug. 18, 2015.

(51) Int. Cl.
  *G06F 19/00* (2018.01)
  *G16H 10/60* (2018.01)
  *G16H 40/20* (2018.01)

(52) U.S. Cl.
  CPC ......... *G06F 19/3481* (2013.01); *G16H 10/60* (2018.01); *G16H 40/20* (2018.01)

(58) Field of Classification Search
  CPC .... G06Q 50/22; G06Q 10/087; G06F 19/322; G06F 19/3406; G06F 19/3481; G16H 10/60; G16H 40/20

(Continued)

(56) References Cited

U.S. PATENT DOCUMENTS 8,156,158 B2   4/2012  Rolls et al.
8,676,600 B2   3/2014  Case et al.
(Continued)

FOREIGN PATENT DOCUMENTS

CN   103793866 A   5/2014

OTHER PUBLICATIONS

Mostafa et al., A Framework for a Smart Social Blood Donation System Based on Mobile Cloud Computing, Nov. 2014, Health Informatics—An International Journal (HIIJ), vol. 3, No. 4, pp. 1-10 (Year: 2014).*

(Continued)

*Primary Examiner* — Joy Chng
(74) *Attorney, Agent, or Firm* — Erik K. Johnson

(57) ABSTRACT

A method for providing cloud-based communication for blood bank collection and management is provided. The method may include detecting and registering a plurality of cloud systems. The method may further include enabling cloud communications for the plurality of cloud systems. Additionally, the method may include receiving at least one blood donation request and blood donation event using the plurality of cloud communications for the plurality of cloud systems. The method may also include recommending and generating lists of blood donors based on the at least one blood donation request and the plurality of cloud systems. The method may further include presenting to users associated with the plurality of cloud systems the at least one blood donation request and blood donation event using the plurality of cloud communications, wherein the users associated with the plurality of cloud systems are based on the plurality of lists of blood donors.

7 Claims, 6 Drawing Sheets

(58) Field of Classification Search
USPC .......................................................... 705/2–3
See application file for complete search history.

(56) References Cited

U.S. PATENT DOCUMENTS

| | | | | |
|---|---|---|---|---|
| 9,294,507 | B1* | 3/2016 | Roth | ........................ H04L 63/20 |
| 2012/0041777 | A1* | 2/2012 | Case | .................... G06Q 10/087 |
| | | | | 705/2 |
| 2014/0279807 | A1* | 9/2014 | Dimitrijevic | .......... G06N 5/025 |
| | | | | 706/47 |

OTHER PUBLICATIONS

Abolghasemi et al., Blood Donor Incentives: A Step Forward or Backward, Jan. 2010, Asian Journal of Transfusion Science, vol. 4, Issue 1, pp. 1-8 (Year: 2010).*

IBM, "List of IBM Patents or Patent Applications Treated as Related (Appendix P)," Aug. 1, 2016, p. 1-2.

Gujarathi et al., "Cloud-Based Blood Bank Collaborative Communication and Recommendation," Application and Drawings, filed Aug. 18, 2016, 34 Pages, U.S. Appl. No. 14/828,576.

Gawali et al., "Location Based Blood Bank Using Cloud Storage," International Journal of Research in IT, Management and Engineering, Mar. 2013, p. 82-88, vol. 3, Issue 3, IJRIME.

Goswami, "Social Media Serves Blood Donation," Taleport Magazine, p. 1-3, https://taleportmagazine.com/how-social-media-serves-blood-donation!, Accessed on Apr. 2, 2015.

Jenipha et al., "Android Blood Donor Life Saving Application in Cloud Computing," American Journal of Engineering Research (AJER), 2014, p. 105-108, vol. 3, Issue 2.

Mell et al., "The NIST Definition of Cloud Computing," National Institute of Standards and Technology, Sep. 2011, p. 1-3, Special Publication 800-145.

Vanitha et al., "BCloud App: Blood Donor Application for Android Mobile," International Journal of Innovations in Engineering and Technology (IJIET), Feb. 2013, p. 396-401, vol. 2, Issue 1.

* cited by examiner

CLOUD-BASED BLOOD BANK COLLABORATIVE COMMUNICATION AND RECOMMENDATION

BACKGROUND

The present invention relates generally to the field of computing, and more specifically, to cloud communication.

Generally, blood banks are useful resources for individuals seeking blood transfusions. Blood banks receive blood via blood donors. Blood donors are typically unpaid volunteers who donate blood for community supply. In some countries, established supplies are limited and donors usually give blood when family or friends need a transfusion. Blood banks generally advertise through online portals to recruit individuals to donate blood. For example, websites may provide individuals with information such as identifying the closest center to an individual's home and giving individuals the opportunity to enroll in mailings and phone calls for reminding the individual of donation opportunities.

SUMMARY

A method for providing cloud-based communication for blood bank collection and management is provided. The method may include detecting a plurality of cloud systems. The method may also include registering the plurality of cloud systems. The method may further include enabling a plurality of cloud communications for the plurality of cloud systems. Additionally, the method may include receiving at least one blood donation request and at least one blood donation event using the plurality of cloud communications for the plurality of cloud systems. The method may also include recommending and generating a plurality of lists of blood donors based on the at least one blood donation request and the plurality of cloud systems. The method may further include presenting to a plurality of users associated with the plurality of cloud systems the at least one blood donation request and the at least one blood donation event using the plurality of cloud communications, wherein the plurality of users associated with the plurality of cloud systems are based on the plurality of lists of blood donors.

A computer system for providing cloud-based communication for blood bank collection and management is provided. The computer system may include one or more processors, one or more computer-readable memories, one or more computer-readable tangible storage devices, and program instructions stored on at least one of the one or more storage devices for execution by at least one of the one or more processors via at least one of the one or more memories, whereby the computer system is capable of performing a method. The method may include detecting a plurality of cloud systems. The method may also include registering the plurality of cloud systems. The method may further include enabling a plurality of cloud communications for the plurality of cloud systems. Additionally, the method may include receiving at least one blood donation request and at least one blood donation event using the plurality of cloud communications for the plurality of cloud systems. The method may also include recommending and generating a plurality of lists of blood donors based on the at least one blood donation request and the plurality of cloud systems. The method may further include presenting to a plurality of users associated with the plurality of cloud systems the at least one blood donation request and the at least one blood donation event using the plurality of cloud communications, wherein the plurality of users associated with the plurality of cloud systems are based on the plurality of lists of blood donors.

A computer program product for providing cloud-based communication for blood bank collection and management is provided. The computer program product may include one or more computer-readable storage devices and program instructions stored on at least one of the one or more tangible storage devices, the program instructions executable by a processor. The computer program product may include program instructions to detect a plurality of cloud systems. The computer program product may also include program instructions to register the plurality of cloud systems. The computer program product may further include program instructions to enable a plurality of cloud communications for the plurality of cloud systems. Additionally, the computer program product may include program instructions to receive at least one blood donation request and at least one blood donation event using the plurality of cloud communications for the plurality of cloud systems. The computer program product may also include program instructions to recommend and generate a plurality of lists of blood donors based on the at least one blood donation request and the plurality of cloud systems. The computer program product may further include program instructions to present to a plurality of users associated with the plurality of cloud systems the at least one blood donation request and the at least one blood donation event using the plurality of cloud communications, wherein the plurality of users associated with the plurality of cloud systems are based on the plurality of lists of blood donors.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
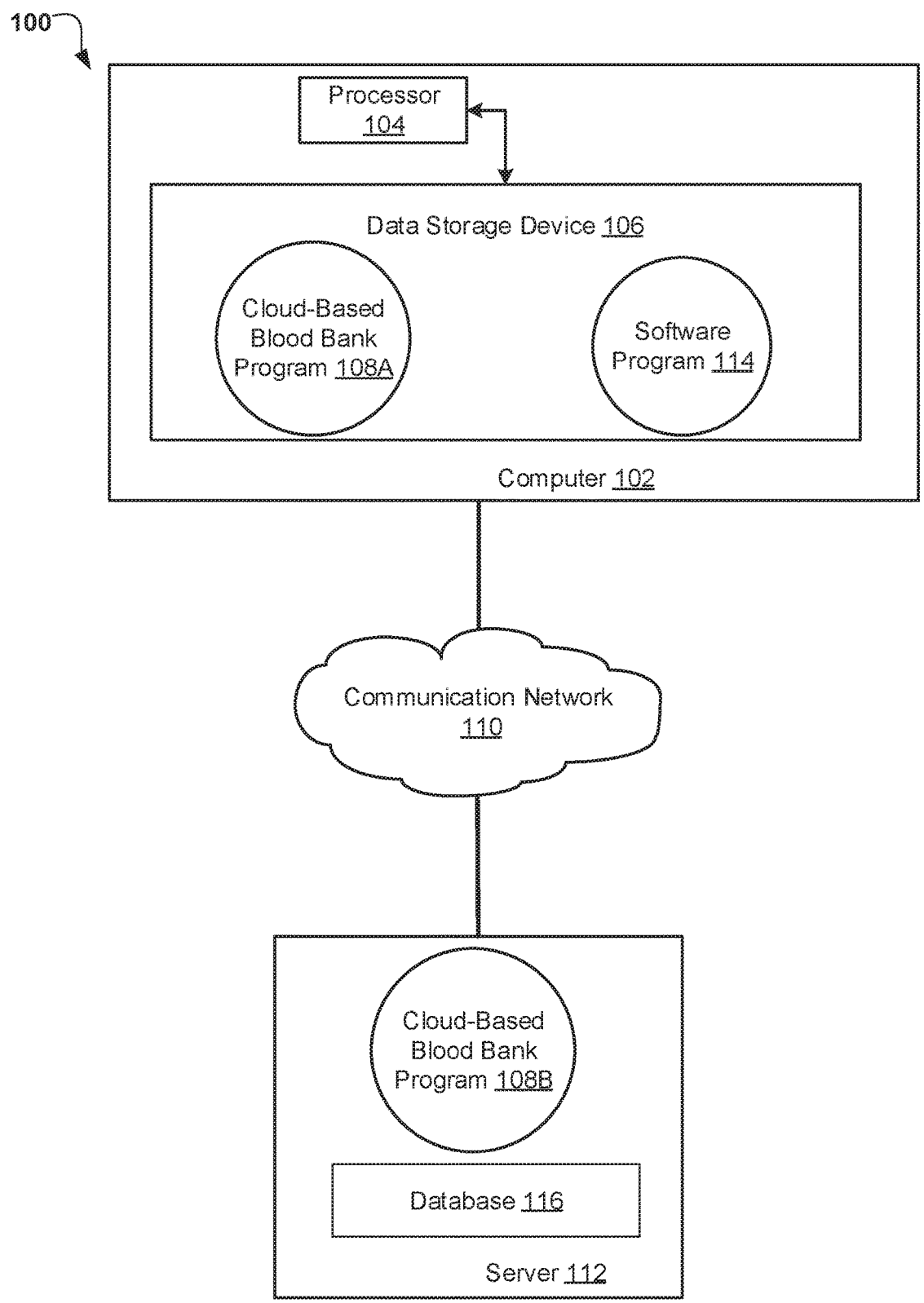
FIG. 1 illustrates a networked computer environment according to one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

Embodiments of the present invention relate generally to the field of computing, and more particularly, to cloud communication. The following described exemplary embodiments provide a system, method and program product for providing a cloud collaborative communication system for presenting blood donation requests and events. Therefore, the present embodiment has the capacity to improve the technical field associated with blood donating by providing a cloud communication network for blood requestors and blood donors. Specifically, the present embodiment may provide a blood bank collaborative communication system to enable cloud communication with blood requestors and blood donors to present blood donation requests and events.

As previously described, blood banks may receive blood via blood donors. Furthermore, blood banks and organizations generally advertise through online portals such as websites to recruit individuals to donate blood. However, such advertisements may be limiting. For example, during medical emergencies it may be difficult to immediately arrange for rare blood groups such as AB Negative, B Negative, O Negative, and AB Positive through advertising. Therefore, blood banks may need an online communication system to accurately locate blood donors and reduce the time it takes to process blood donation requests. As such, it may be advantageous, among other things, to provide a system, method and program product for providing cloud-based communication for blood bank collection and management. Specifically, users and administrators may expedite the processing of blood donation requests by soliciting and communicating with blood donors using cloud communication tools.

According to at least one implementation of the present embodiment, cloud systems may be detected and registered. Then, cloud-based communications for the cloud systems may be enabled. Next, at least one blood donation request and/or blood donation event may be received. Then, based on the received blood donation requests and blood donation events, lists of blood donors and users may be recommended and generated. Thereafter, the blood donation requests and blood donation events, along with blood donation benefits, may be presented to users and blood donors.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for providing cloud-based communication for blood bank collection and management.

According to at least one implementation, cloud systems may be detected and registered. Then, cloud-based communications for the cloud systems may be enabled. Next, at least one blood donation request and/or blood donation event may be received. Then, based on the received blood donation requests and blood donation events, lists of blood donors and users may be recommended and generated. Thereafter, the blood donation requests and blood donation events, along with blood donation benefits, may be presented to users and blood donors.

Referring now to FIG. 1, an exemplary networked computer environment 100 in accordance with one embodiment is depicted. The networked computer environment 100 may include a computer 102 with a processor 104 and a data storage device 106 that is enabled to run a cloud-based blood bank program 108A and a software program 114. The software program 114 may be an application program such as an internet browser and an email program. The cloud-based blood bank program 108A may communicate with the software program 114. The networked computer environment 100 may also include a server 112 that is enabled to run a cloud-based blood bank program 108B and a communication network 110. The networked computer environment 100 may include a plurality of computers 102 and servers 112, only one of which is shown for illustrative brevity.

According to at least one implementation, the present embodiment may also include a database 116, which may be running on server 112. The communication network may include various types of communication networks, such as a wide area network (WAN), local area network (LAN), a telecommunication network, a wireless network, a public switched network and/or a satellite network. It may be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with server computer 112 via the communications network 110. The communications network 110 may include connections, such as wire, wireless communication links, or fiber optic cables. As will be discussed with reference to FIG. 4, server computer 112 may include internal components 800a and external components 900a, respectively and client computer 102 may include internal components 800b and external components 900b, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing device capable of running a program and accessing a network. According to various implementations of the present embodiment, the cloud-based blood bank program 108A, 108B may interact with a database 116 that may be embedded in various storage devices, such as, but not limited to a mobile device 102, a networked server 112, or a cloud storage service.

According to the present embodiment, a program, such as a cloud-based blood bank program 108A and 108B may run on the client computer 102 or on the server computer 112 via a communications network 110. The cloud-based blood bank program 108A, 108B may enable cloud-based communications to process blood donation requests and events. Specifically, a user using a computer, such as computer 102, may run a cloud-based blood bank program 108A, 108B, that interacts with a software program 114, such as Firefox® (Firefox and all Firefox-based trademarks and logos are trademarks or registered trademarks of Firefox and/or its affiliates) to provide cloud-based communication for blood requestors and blood donors, to receive blood donation requests and events, and to present the blood donation requests and events to the cloud users.

Figure 2:
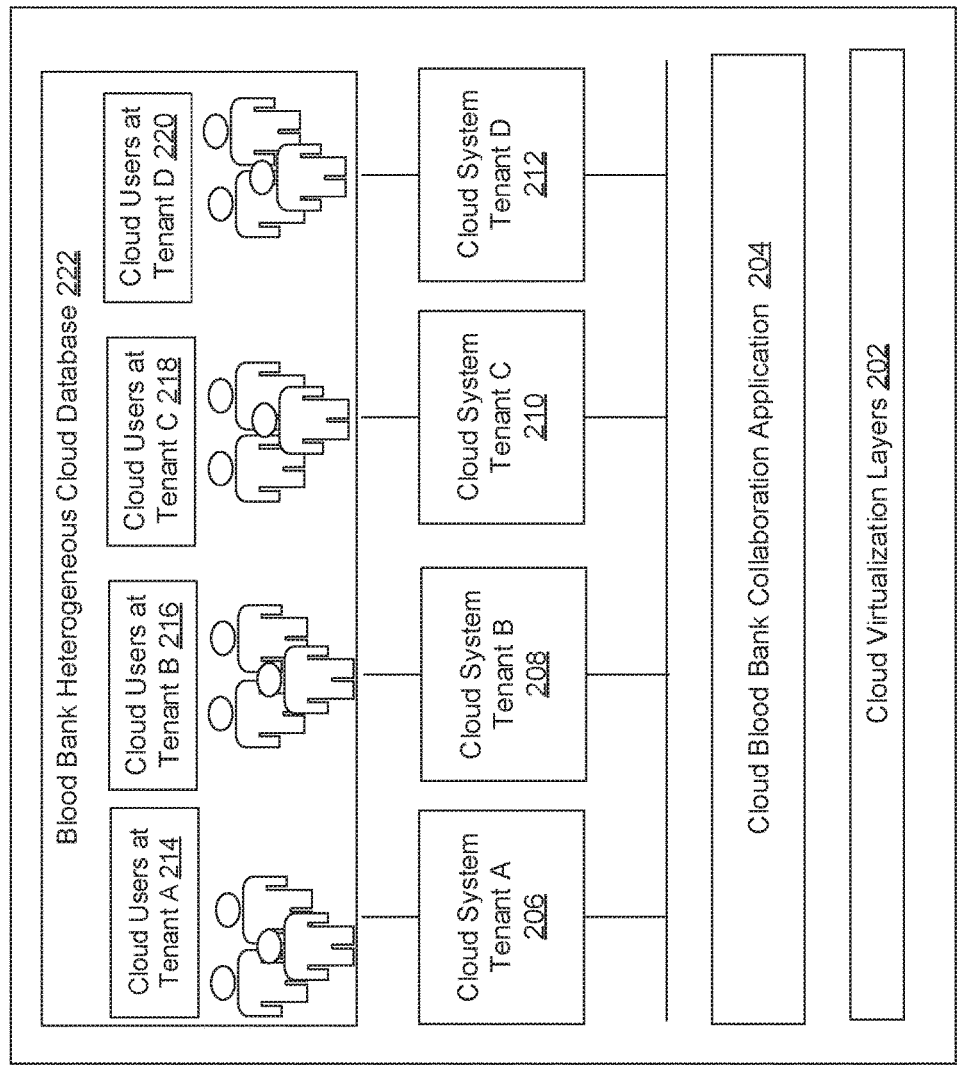
FIG. 2 is block diagram illustrative of a cloud-based blood bank program 108A, 108B in accordance with one embodiment according to one embodiment.

Referring now to FIG. 2, a block diagram 200 illustrative of a cloud-based blood bank program 108A, 108B (FIG. 1) in accordance with one embodiment is depicted. As previously described in FIG. 1, the cloud-based blood bank program 108A, 108B (FIG. 1) may enable cloud-based communications associated with a plurality of cloud administrators and users to receive blood donation requests and events. Specifically, the cloud-based blood bank program 108A, 108B (FIG. 1) may include cloud virtualization layers 202 to initiate a blood bank collaboration application 204. Furthermore, using the cloud blood bank collaboration application 204, the cloud-based blood bank program 108A, 108B (FIG. 1) may enable cloud users 214, 216, 218, and 220 to communicate and access information associated with cloud systems, such as cloud systems 206, 208, 210, and 212. According to one implementation, the cloud users 214, 216, 218, and 220 may include blood donors. Also, according to one implementation, the cloud systems 206, 208, 210, and 212 may include databases that stores information on blood donors and events related to blood donating. For example, the cloud systems 206, 208, 210, and 212 may include information on blood donors such as the type of blood for each blood donor, relatives of the blood donors, the medical history of the blood donors, and the location of the blood donors. Furthermore, the cloud systems 206, 208, 210, and 212 may include events and information related to blood donating such as blood donation drives, blood donation sites, and blood donor incentives and benefits. Additionally, according to one implementation, the cloud-based blood bank program 108A, 108B (FIG. 1) may use unique identifiers to encrypt the blood donation information associated with the blood donors and blood requestors.

Also, according to one implementation, the cloud-based blood bank program 108A, 108B (FIG. 1) may enable and restrict user access to the information associated with cloud systems 206, 208, 210, and 212. Specifically, the cloud systems 206, 208, 210, and 212 may include public cloud systems, private cloud systems, and hybrid cloud systems, as well as cloud administrators for the cloud systems 206, 208, 210, and 212. For example, the cloud-based blood bank program 108A, 108B (FIG. 1) may include a private cloud system Tenant "A" 206, wherein the information associated with the private cloud system Tenant "A" 206 is accessible to cloud users at Tenant "A" 214 but inaccessible to cloud users at Tenant "B" 216, Tenant "C" 218, and Tenant "D" 220. Furthermore, the cloud-based blood bank program 108A, 108B (FIG. 1) may include a public cloud system Tenant "B" 208, wherein the information associated with the public cloud system Tenant "B" 208 is accessible by cloud users at Tenant "A" 214, Tenant "B" 216, Tenant "C" 218, and Tenant "D" 220. Additionally, the cloud-based blood bank program 108A, 108B (FIG. 1) may include a hybrid cloud system Tenant "C" 210, wherein the hybrid cloud system Tenant "C" 210 may include information that is accessible as well as information that is inaccessible by cloud users at Tenant "A" 214, Tenant "B" 216, Tenant "C" 218, and Tenant "D" 220. Also, according to one embodiment, the cloud-based blood bank program 108A, 108B (FIG. 1) may enable access to the information associated with the cloud systems 206, 208, 210, and 212 by registering user identification information and verifying credentials based on the registration information.

Furthermore, according to one implementation, the cloud-based blood bank program 108A, 108B may include a blood bank heterogeneous cloud database 222. Specifically, according to one implementation, the blood bank heterogeneous cloud database 222 may be a public cloud system that is synced to the cloud systems 206, 208, 210, and 212. Furthermore, based on the type of cloud system 206, 208, 210, and 212, the blood bank heterogeneous cloud database 222 may publicly store and enable access to the blood donation information and events that are associated with the information stored on the cloud systems 206, 208, 210, and 212. For example, the cloud-based blood bank program 108A, 108B (FIG. 1) may include a hybrid cloud system Tenant "C" 210 having information that is accessible as well as information that is inaccessible by cloud users 214, 216, 218, and 220. Therefore, the blood bank heterogeneous cloud database 222 may store and enable access to the accessible information associated with the hybrid cloud system Tenant "C" 210. As such, using the blood bank heterogeneous cloud database 222, the cloud-based blood bank program 108A, 108B (FIG. 1) may enable cloud administrators and cloud users 214, 216, 218, and 220 to share and access the information associated with the cloud systems 206, 208, 210, and 212.

Figure 3:
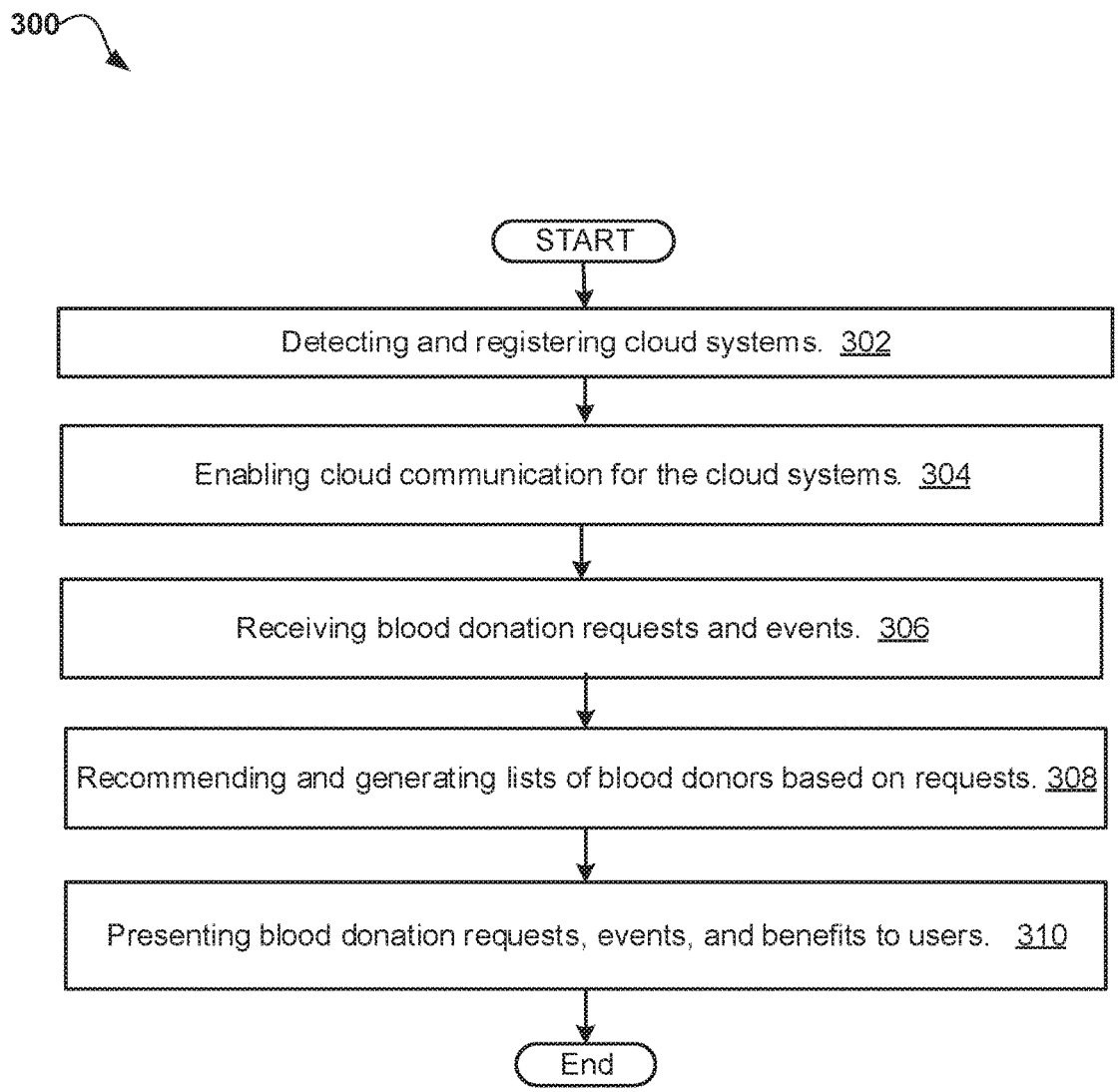
FIG. 3 is an operational flowchart illustrating the steps carried out by a program for providing cloud-based communication for blood bank collection and management according to one embodiment.

Referring now to FIG. 3, an operational flowchart 300 illustrating the steps carried out by a program for providing cloud-based communication for blood bank collection and management is depicted. At 302, the cloud-based blood bank program 108A, 108B (FIG. 1) may detect and register cloud systems 206, 208, 210, and 212 (FIG. 2), cloud administrators, and cloud users 214, 216, 218, and 220 (FIG. 2). Specifically, according to one embodiment, the cloud-based blood bank program 108A, 108B (FIG. 1) may detect and register information associated with the cloud systems 206, 208, 210, and 212 (FIG. 2), as well as detect and register cloud administrators and cloud users 214, 216, 218, and 220 (FIG. 2) associated with the cloud systems 206, 208, 210, and 212 (FIG. 2). For example, the cloud-based blood bank program 108A, 108B (FIG. 1) may detect the cloud system Tenant "B" 208 (FIG. 2), and register information associated with the cloud system Tenant "B" 208 (FIG. 2). Specifically, the cloud-based blood bank program 108A, 108B (FIG. 1) may detect and register such information as whether the cloud system Tenant "B" 208 (FIG. 2) is a public, private, or hybrid cloud system, as well as detect and register the cloud databases associated with the cloud system Tenant "B" 208 (FIG. 2) and the cloud administrators and cloud users 214, 216, 218, and 220 (FIG. 2) associated with the cloud system Tenant "B" 208 (FIG. 2).

At 304, the cloud-based blood bank program 108A, 108B (FIG. 1) may enable cloud communication for the cloud systems 206, 208, 210, and 212 (FIG. 2). As previously described at step 302, the cloud-based blood bank program 108A, 108B (FIG. 1) may detect and register the cloud systems 206, 208, 210, and 212 (FIG. 2), as well as the associated cloud administrators and cloud users 214, 216, 218, and 220 (FIG. 2). As such, the cloud-based blood bank program 108A, 108B (FIG. 1) may then enable the cloud administrators and cloud users 214, 216, 218, and 220 (FIG. 2) to communicate and access information associated with the cloud systems 206, 208, 210, and 212 (FIG. 2). Specifically, and as previously described in FIG. 2, the cloud-based blood bank program 108A, 108B (FIG. 1) may include cloud virtualization layers 202 (FIG. 2) to initiate a cloud blood bank collaboration application 204 (FIG. 2). Then, using the cloud blood bank collaboration application 204 (FIG. 2), the cloud-based blood bank program 108A, 108B (FIG. 1) may enable cloud administrators and cloud users 214, 216, 218, and 220 (FIG. 2) to communicate using communication tools such as email, chat, forums, conferencing, instant messaging, and voice over internet protocol (VoIP). For example, the cloud-based blood bank program 108A, 108B (FIG. 1) may enable cloud administrators and cloud users at Tenant "A" 214 (FIG. 2) to communicate with cloud administrators and cloud users at Tenant "B" 216 (FIG. 2), Tenant "C" 218 (FIG. 2), and Tenant "D" 220 (FIG. 2).

Additionally, the cloud-based blood bank program 108A, 108B (FIG. 1) may enable cloud administrators and cloud users 214, 216, 218, and 220 (FIG. 2) to access information associated with the cloud systems 206, 208, 210, and 212 (FIG. 2). As previously described in FIG. 2, the cloud-based blood bank program 108A, 108B (FIG. 1) may include a blood bank heterogeneous cloud database 222 (FIG. 2). Specifically, according to one implementation, the blood bank heterogeneous cloud database 222 (FIG. 2) may be a public cloud system that is synced with the cloud systems 206, 208, 210, and 212 (FIG. 2), and that publicly stores blood donation information and events that are associated with the blood donation information stored on the cloud systems 206, 208, 210, and 212 (FIG. 2). Therefore, using the blood bank heterogeneous cloud database 222 (FIG. 2), the cloud-based blood bank program 108A, 108B (FIG. 1) may enable cloud administrators and cloud users 214, 216, 218, and 220 (FIG. 2) to share and access the information associated with the cloud systems 206, 208, 210, and 212 (FIG. 2). Furthermore, according to one implementation, the cloud-based blood bank program 108A, 108B (FIG. 1) may use unique identifiers to encrypt the blood donation information associated with blood donors and blood requestors.

Then, at 306, the cloud-based blood bank program 108A, 108B (FIG. 1) may receive blood donation requests and events. As previously described at step 304, the cloud-based blood bank program 108A, 108B (FIG. 1) may enable cloud administrators and cloud users 214, 216, 218, and 220 (FIG. 2) to communicate. Specifically, the cloud-based blood bank program 108A, 108B (FIG. 1) may enable cloud administrators and cloud users 214, 216, 218, and 220 (FIG. 2) to request blood donors to donate blood and publicize blood donation events using communication tools such as email, chat, forums, conferencing, instant messaging, and voice over internet protocol (VoIP). For example, the cloud-based blood bank program 108A, 108B (FIG. 1) may receive forum postings initiated by cloud administrators requesting blood donors compatible with the blood type A+ to donate blood, as well as receive publications for blood donation drives at different locations.

Also, according to one implementation, the cloud-based blood bank program 108A, 108B (FIG. 1) may categorize blood donation requests as sensitive, and designate the sensitive blood donation requests for selected cloud administrators and users 214, 216, 218, and 220 (FIG. 2). For example, the cloud-based blood bank program 108A, 108B (FIG. 1) may receive a blood donation request for an HIV infected person. As such, the cloud-based blood bank program 108A, 108B (FIG. 1) may categorize the blood donation request for the HIV infected person as sensitive, then may designate the sensitive blood donation request for the HIV infected person for selected cloud administrators associated with the cloud systems 206, 208, 210, and 212 (FIG. 2) that may have HIV infected cloud users 214, 216, 216, and 220 (FIG. 2) and/or users interested in giving blood to HIV infected persons.

Next, at 308, the cloud-based blood bank program 108A, 108B (FIG. 1) may recommend and generate lists of blood donors based on the blood donation requests. As previously described at step 306, the cloud-based blood bank program 108A, 108B (FIG. 1) may receive and display blood donation requests and events to cloud administrators and cloud users 214, 216, 216, and 220 (FIG. 2). As such, based on the blood donation requests, the cloud-based blood bank program 108A, 108B (FIG. 1) may recommend and generate lists of potential blood donors according to information associated with the blood requestors and blood donors that is stored on the blood bank heterogeneous cloud database 222 (FIG. 2) and cloud system 206, 208, 210, and 212 (FIG. 2).

Specifically, the cloud-based blood bank program 108A, 108B (FIG. 1) may recommend blood donors based on such information as the type of blood requested, the relatives of the blood requestors and blood donors, the medical history of the blood requestors and blood donors, the location of the blood requestors and blood donors, and the amount of times blood donors have donated. For example, the cloud-based blood bank program 108A, 108B (FIG. 1) may receive forum postings initiated by cloud administrators requesting blood donors who are compatible with the blood type A+ to donate blood. Thereafter, the cloud-based blood bank program 108A, 108B (FIG. 1) may recommend blood donors who are compatible with the blood type A+, blood donors who are ranked based on received points, blood donors who are related to the blood requestor, and blood donors located near the blood requestor.

Then, at 310, the cloud-based blood bank program 108A, 108B (FIG. 1) may present the blood donation requests and events to the lists of blood donors. As previously described at step 308, the cloud-based blood bank program 108A, 108B (FIG. 1) may recommend and generate lists of blood donors based information related to the blood requestors and blood donors. Furthermore, and as previously described in FIG. 2, the cloud users 214, 216, 218, and 220 (FIG. 2) may include blood donors. As such, the cloud-based blood bank program 108A, 108B (FIG. 1) may present the blood donation requests to the lists of blood donors using the cloud communication tools. Specifically, using cloud communication tools such as such as email, chat, forums, conferencing, instant messaging, and voice over internet protocol (VoIP), the cloud-based blood bank program 108A, 108B (FIG. 1) may present the blood donation requests to cloud users 214, 216, 218, and 220 (FIG. 2). Furthermore, the cloud-based blood bank program 108A, 108B (FIG. 1) may present cloud users 214, 216, 218, and 220 (FIG. 2) with blood donation events such as the nearest blood drive to donate blood, and benefits and incentives for donating blood. For example, the cloud-based blood bank program 108A, 108B (FIG. 1) may recommend a list of blood donors who are compatible with the blood type A+ and who live near the blood requestor. Therefore, the cloud-based blood bank program 108A, 108B (FIG. 1) may generate emails and/or instant messages, that may include the blood requestor information as well as blood donation sites, to the cloud users 214, 216, 218, and 220 (FIG. 2) associated with the generated list of blood donors.

It may be appreciated that FIGS. 2 and 3 provide only illustrations of one implementation and does not imply any limitations with regard to how different embodiments may be implemented. Many modifications to the depicted environments may be made based on design and implementation requirements. Specifically, according to one implementation, the cloud-based blood bank program 108A, 108B (FIG. 1) may enable a social pyramid network and rank blood donors based on points associated with the social pyramid network, whereby blood donors in the social pyramid network receive points for donating blood and thereby gain in rank in the social pyramid network for each blood donation. Therefore, the cloud-based blood bank program 108A, 108B (FIG. 1) may recommend blood donors based on a trust that is established with blood donors by ranking the blood donors in the social pyramid network.

Also, for example, at step 310 (FIG. 3), the cloud-based blood bank program 108A, 108B (FIG. 1) may present incentives and benefits information to cloud administrators and cloud users 214, 216, 218, and 220 (FIG. 2) who have rare blood group types. Specifically, based on information stored at the cloud systems 206, 208, 210, and 212 (FIG. 2), the cloud-based blood bank program 108A, 108B (FIG. 1) may detect statistics such as whether selected blood group types are scarce in different areas, and whether selected nationalities are lacking blood group types based on the compositions of blood specific to the nationalities. Therefore, the cloud-based blood bank program 108A, 108B (FIG. 1) may present incentives and benefits information to cloud administrators and cloud users 214, 216, 218, and 220 (FIG. 2) who have rare blood groups to entice such cloud administrators and cloud users 214, 216, 218, and 220 (FIG. 2) to move to the scarcity zones, or the areas lacking the blood group types. For example, the cloud-based blood bank program 108A, 108B (FIG. 1) may detect that a selected area is lacking the rare blood type O+. As such, the cloud-based blood bank program 108A, 108B (FIG. 1) may present incentives and benefits information, such as marriage benefits and tax benefits, to cloud users 214, 216, 218, and 220 (FIG. 2) with blood types compatible to blood type O+ that are willing to move to and marry in the selected area lacking the rare blood type O+. As such, the cloud-based blood bank program 108A, 108B (FIG. 1) may promote cloud users 214, 216, 218, and 220 (FIG. 2) migration to scarcity areas to counterbalance scarcity of blood groups.

Figure 4:
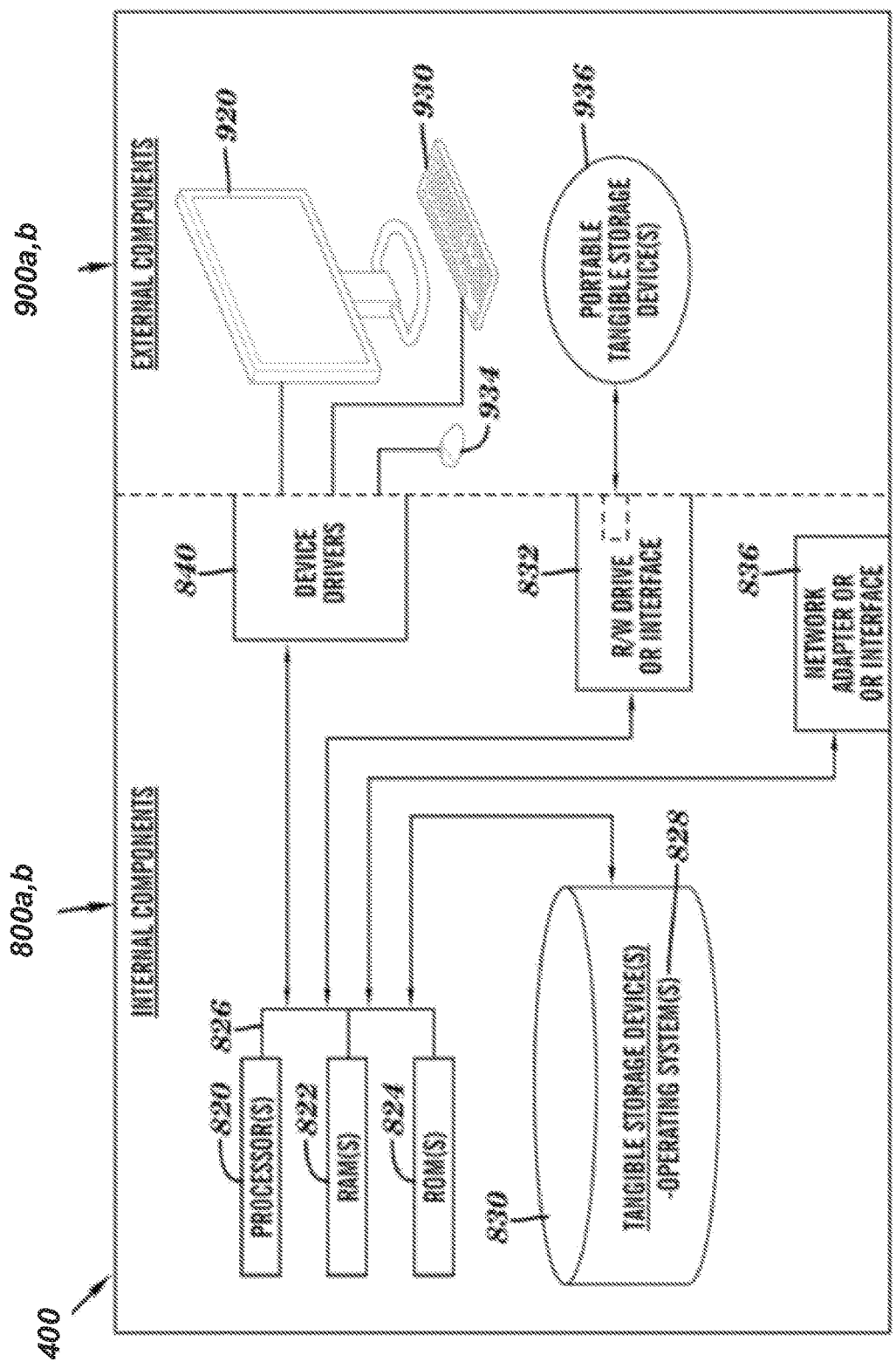
FIG. 4 is a block diagram of the system architecture of a program for providing cloud-based communication for blood bank collection and management according to one embodiment.

FIG. 4 is a block diagram 400 of internal and external components of computers depicted in FIG. 1 in accordance with an illustrative embodiment of the present invention. It should be appreciated that FIG. 4 provides only an illustration of one implementation and does not imply any limitations with regard to the environments in which different embodiments may be implemented. Many modifications to the depicted environments may be made based on design and implementation requirements.

Data processing system 800, 900 is representative of any electronic device capable of executing machine-readable program instructions. Data processing system 800, 900 may be representative of a smart phone, a computer system, PDA, or other electronic devices. Examples of computing systems, environments, and/or configurations that may represented by data processing system 800, 900 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 (FIG. 1), and network server 112 (FIG. 1) include respective sets of internal components 800 a, b and external components 900 a, b illustrated in FIG. 4. Each of the sets of internal components 800 a, b includes one or more processors 820, one or more computer-readable RAMs 822 and one or more computer-readable ROMs 824 on one or more buses 826, and one or more operating systems 828 and one or more computer-readable tangible storage devices 830. The one or more operating systems 828, the software program 114 (FIG. 1), the cloud-based blood bank program 108A (FIG. 1) in client computer 102 (FIG. 1), and the cloud-based blood bank program 108B (FIG. 1) in network server computer 112 (FIG. 1) are stored on one or more of the respective computer-readable tangible storage devices 830 for execution by one or more of the respective processors 820 via one or more of the respective RAMs 822 (which typically include cache memory). In the embodiment illustrated in FIG. 4, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory or any other computer-readable tangible storage device that can store a computer program and digital information.

Each set of internal components 800 a, b, also includes a R/W drive or interface 832 to read from and write to one or more portable computer-readable tangible storage devices 936 such as a CD-ROM, DVD, memory stick, magnetic tape, magnetic disk, optical disk or semiconductor storage device. A software program, such as a cloud-based blood bank program 108A and 108B (FIG. 1), can be stored on one or more of the respective portable computer-readable tangible storage devices 936, read via the respective R/W drive or interface 832 and loaded into the respective hard drive 830.

Each set of internal components 800 a, b also includes network adapters or interfaces 836 such as a TCP/IP adapter cards, wireless Wi-Fi interface cards, or 3G or 4G wireless interface cards or other wired or wireless communication links. The cloud-based blood bank program 108A (FIG. 1) and software program 114 (FIG. 1) in client computer 102 (FIG. 1), and the cloud-based blood bank program 108B (FIG. 1) in network server 112 (FIG. 1) can be downloaded to client computer 102 (FIG. 1) from an external computer via a network (for example, the Internet, a local area network or other, wide area network) and respective network adapters or interfaces 836. From the network adapters or interfaces 836, the cloud-based blood bank program 108A (FIG. 1) and software program 114 (FIG. 1) in client computer 102 (FIG. 1) and the cloud-based blood bank program 108B (FIG. 1) in network server computer 112 (FIG. 1) are loaded into the respective hard drive 830. The network may comprise copper wires, optical fibers, wireless transmission, routers, firewalls, switches, gateway computers and/or edge servers.

Each of the sets of external components 900 a, b can include a computer display monitor 920, a keyboard 930, and a computer mouse 934. External components 900 a, b can also include touch screens, virtual keyboards, touch pads, pointing devices, and other human interface devices. Each of the sets of internal components 800 a, b also includes device drivers 840 to interface to computer display monitor 920, keyboard 930 and computer mouse 934. The device drivers 840, R/W drive or interface 832 and network adapter or interface 836 comprise hardware and software (stored in storage device 830 and/or ROM 824).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 5:
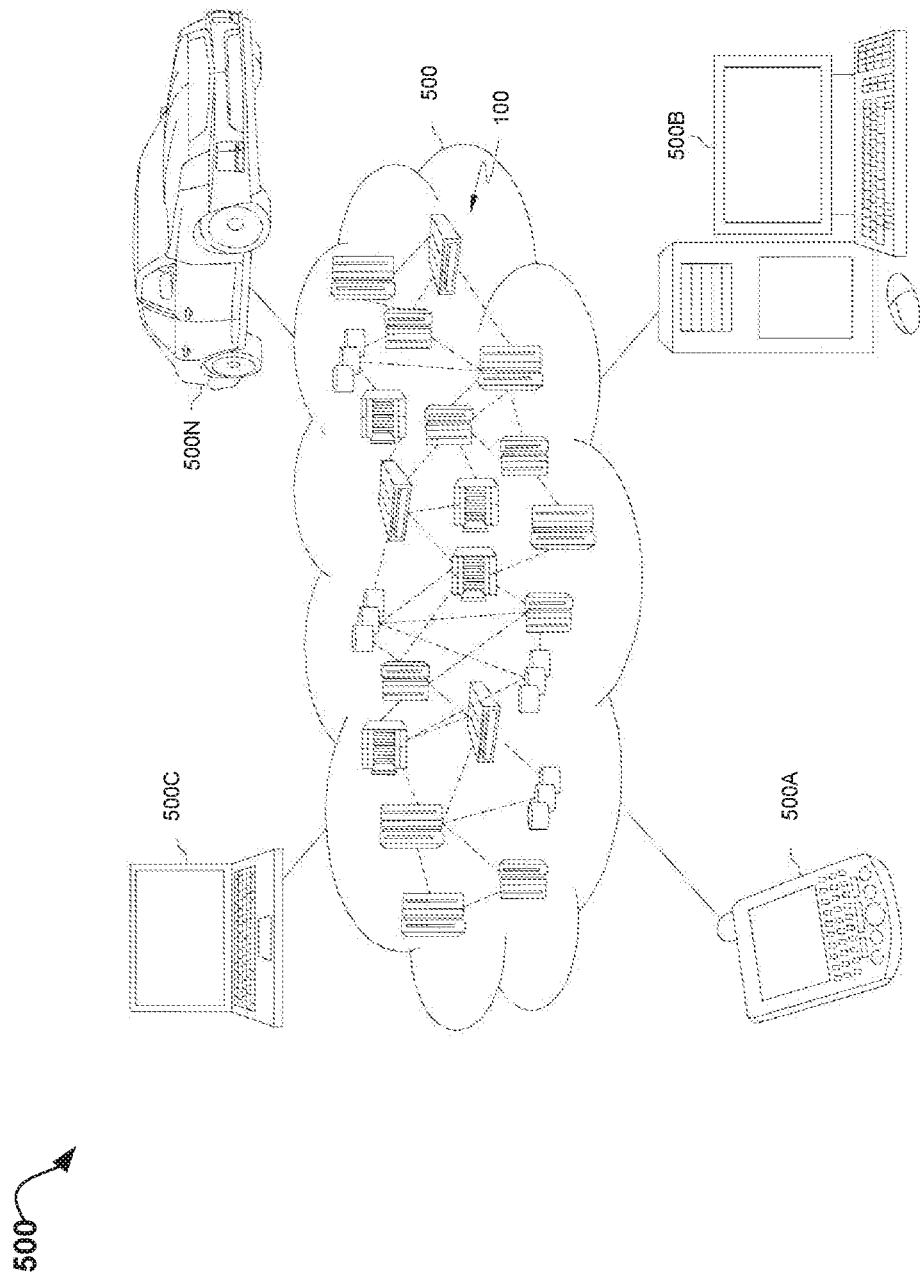
FIG. 5 is a block diagram of an illustrative cloud computing environment including the computer system depicted in FIG. 1, in accordance with an embodiment of the present disclosure.

Referring now to FIG. 5, illustrative cloud computing environment 500 is depicted. As shown, cloud computing environment 500 comprises one or more cloud computing nodes 100 with which local computing devices used by cloud consumers, such as, for example, personal digital assistant (PDA) or cellular telephone 500A, desktop computer 500B, laptop computer 500C, and/or automobile computer system 500N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 500 to offer infrastructure, platforms and/or software as services for which a cloud consumer does not need to maintain resources on a local computing device. It is understood that the types of computing devices 500A-N shown in FIG. 5 are intended to be illustrative only and that computing nodes 100 and cloud computing environment 500 can communicate with any type of computerized device over any type of network and/or network addressable connection (e.g., using a web browser).

Figure 6:
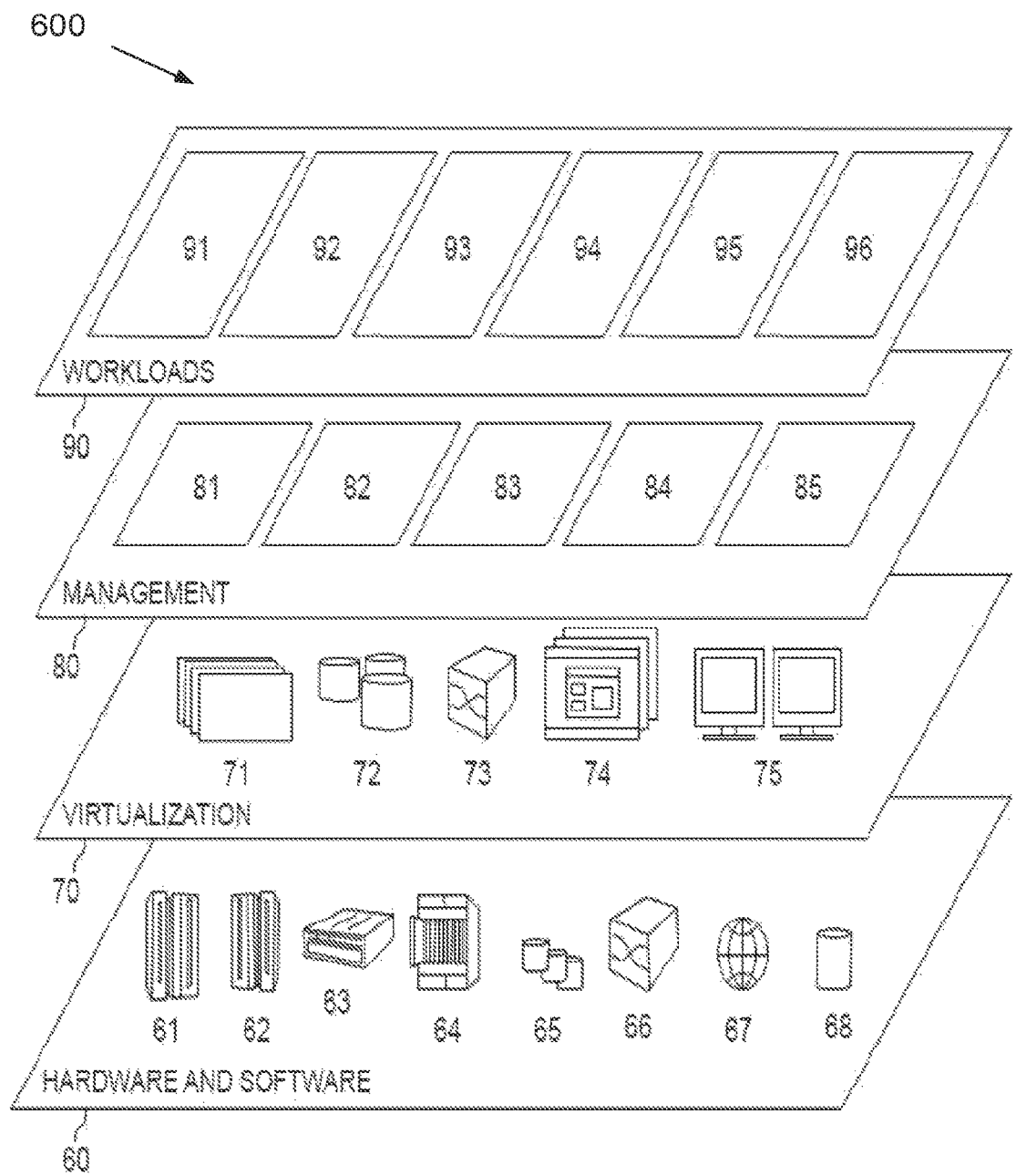
FIG. 6 is a block diagram of functional layers of the illustrative cloud computing environment of FIG. 5, in accordance with an embodiment of the present disclosure.

Referring now to FIG. 6, a set of functional abstraction layers 600 provided by cloud computing environment 500 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and Cloud-Based Blood Bank 96. A Cloud-Based Blood Bank Program 108A, 108B (FIG. 1) may be offered "as a service in the cloud" (i.e., Software as a Service (SaaS)) for applications running on mobile devices 102 (FIG. 1) and may provide cloud-based communication for cloud systems for blood bank collection and management.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for providing cloud-based communication for blood bank collection and management, comprising:

detecting a plurality of cloud systems;

registering the detected plurality of cloud systems based on a type of cloud system associated with the detected plurality of cloud systems;

enabling a plurality of cloud communications for the registered plurality of cloud systems, wherein enabling a plurality of cloud communications for the registered plurality of cloud systems comprises restricting user access to information associated with one or more cloud systems that are associated with the registered plurality of cloud systems based on the type of the cloud system;

enabling a blood bank cloud database, wherein the blood bank cloud database stores the information associated with the registered plurality of cloud systems, and wherein the information on the blood bank cloud database is restricted based on the type of the cloud system associated with the information;

receiving at least one blood donation request and at least one blood donation event using the enabled plurality of cloud communications for the registered plurality of cloud systems;

in response to receiving the at least one blood donation request, categorizing the at least one blood donation request based on information associated with the at least one blood donation request, and designating the at least one blood donation request for selected cloud administrators and users based on the categorization of the at least one blood donation request, wherein the categorization is based on a determination that there is sensitive information associated with the at least one blood donation request;

generating a plurality of lists of blood donors based on the at least one blood received donation request and the registered plurality of cloud systems; and presenting to a plurality of users associated with the registered plurality of cloud systems, the generated at least one blood donation request based on the categorization and the received at least one blood donation event using the enabled plurality of cloud communications, wherein the plurality of users associated with the registered plurality of cloud systems are based on the generated plurality of lists of blood donors.

2. The method of claim 1, wherein the registered plurality of cloud systems comprises a plurality of cloud databases, a plurality of cloud administrators, and a plurality of cloud users.

3. The method of claim 1, further comprising:

storing a plurality of blood donor information associated with the registered plurality of cloud systems in a blood bank heterogeneous database.

4. The method of claim 1, wherein the enabled plurality of cloud communications comprises at least one of an email message, a conference, a chat, an instant message, a forum post, and a voice over internet protocol (VoIP).

5. The method of claim 1, wherein the received at least one blood donation event comprises at least one of a plurality of blood donation drives, a plurality of blood donation sites, and a plurality of blood donation benefits.

6. The method of claim 5, wherein the generated plurality of lists of blood donors are based on at least one of a blood group compatibility, a familial relationship, a global positioning satellite (GPS) location, and a social pyramid network associated with a blood donation points ranking.

7. The method of claim 5, further comprising:

detecting at least one statistic associated with at least one blood group in a plurality of areas, wherein the at least one statistic comprises at least one of a scarcity level measurement and a nationality measurement; and recommending and presenting a plurality of benefits to a plurality of blood donors compatible with the at least one blood group based on the at least one statistic, wherein the plurality of benefits comprises at least one of a marriage benefit and a tax benefit.

* * * * *